United States Patent
Hasegawa

(10) Patent No.: US 8,594,595 B2
(45) Date of Patent: Nov. 26, 2013

(54) WIRELESS TERMINAL CAPABLE OF SUPPRESSING THE POWER CONSUMPTION OF A MAIN POWER SUPPLY UNIT

(75) Inventor: Yasuhiro Hasegawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 12 days.

(21) Appl. No.: 13/334,554

(22) Filed: Dec. 22, 2011

(65) Prior Publication Data

US 2012/0184230 A1    Jul. 19, 2012

(30) Foreign Application Priority Data

Jan. 17, 2011    (JP) .................... 2011-006952

(51) Int. Cl.
*H04B 1/04*    (2006.01)
*H04B 7/00*    (2006.01)

(52) U.S. Cl.
USPC .................... 455/127.1; 455/41.2

(58) Field of Classification Search
USPC ............. 455/41.2, 343.5, 522, 41.1, 343.1, 455/127.1, 127.5; 340/539.12, 539.3; 607/29, 60
See application file for complete search history.

(56) References Cited

U.S. PATENT DOCUMENTS

| | | | | |
|---|---|---|---|---|
| 5,974,327 A | * | 10/1999 | Agrawal et al. | 455/452.2 |
| 6,108,316 A | * | 8/2000 | Agrawal et al. | 370/311 |
| 6,577,901 B2 | * | 6/2003 | Thompson | 607/60 |
| 6,671,552 B2 | * | 12/2003 | Merritt et al. | 607/29 |
| 7,800,494 B2 | * | 9/2010 | Kim | 340/539.12 |
| 2011/0202730 A1 | * | 8/2011 | Sonoda et al. | 711/141 |

FOREIGN PATENT DOCUMENTS

JP    8-069513 A    3/1996

* cited by examiner

*Primary Examiner* — Sonny Trinh
(74) *Attorney, Agent, or Firm* — Westerman, Hattori, Daniels & Adrian, LLP

(57) ABSTRACT

A wireless terminal may include a sensor unit that generates data, a wireless communication unit that wirelessly transmits the data, a main power supply unit that supplies power to the sensor unit and the wireless communication unit, a determination unit that determines a level of transmission urgency of wireless transmission of the data; and a control unit that controls the wireless communication unit to wirelessly transmit the data, the control unit executing control to inhibit the wireless communication unit from using power supplied from the main power supply unit when causing the wireless communication unit to wirelessly transmit the data of which the transmission urgency is determined to be low by the determination unit.

6 Claims, 8 Drawing Sheets

| DETERMINATION RESULT | RETENTION UNIT | POWER SWITCHING UNIT |
|---|---|---|
| URGENT TRANSMISSION INDICATION | DATA OUTPUT | BATTERY SELECTION |
| POWER-SAVING TRANSMISSION INDICATION | DATA OUTPUT | POWER GENERATING UNIT SELECTION |
| TRANSMISSION-CANCEL INDICATION | DATA DELETION | — |

# WIRELESS TERMINAL CAPABLE OF SUPPRESSING THE POWER CONSUMPTION OF A MAIN POWER SUPPLY UNIT

BACKGROUND OF THE INVENTION

1. Field of the Invention

The present invention relates to a wireless terminal.

Priority is claimed on Japanese Patent Application No. 2011-006952, filed Jan. 17, 2011, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In the medical and healthcare fields, efforts to make biological data stored by a storage device useful for health management, disease diagnosis, treatment, or the like by collecting the biological data from the surface of a human body or an inside of a human body using a terminal having various sensors and transferring the biological data collected by the terminal to the storage device are ongoing. Because the freedom of movement is limited when a wired cable is connected between the terminal for transferring the biological data and the storage device for the above-described purpose, it is preferable to transfer the biological data by wireless communication and freely carry the terminal. The above-described need is larger in medical fields, particularly, implantable medical devices.

In general, the implantable medical device operates by obtaining power from a battery. Accordingly, it is necessary to replace the battery when battery power is consumed and a voltage is lowered. Because surgery is necessary to replace the battery of the implantable medical device, a burden on a patient may be increased, and side effects such as infection may also occur, it is preferable to avoid the consumption of battery power as much as possible. For the above-described requirement, studies on technology for generating power from vibration, a temperature difference, light, electromagnetic waves, or the like are ongoing. An example of a product of a combination of wireless communication technology and technology for generating power from the electromagnetic waves may be a non-contact integrated circuit (IC) card. In addition, a non-contact IC card that can lengthen the life of a primary battery by embedding the primary battery and a storage capacitor for rectifying and storing energy of the electromagnetic waves, using the power of the storage capacitor when received electromagnetic waves are strong, and using and operating the primary battery when the received electromagnetic waves are weak is known (see Japanese Unexamined Patent Application, First Publication No. H8-69513).

SUMMARY

The present invention provides a wireless terminal capable of further suppressing the power consumption of a main power supply unit such as a primary battery.

A wireless terminal may include: a sensor unit that generates data; a wireless communication unit that wirelessly transmits the data; a main power supply unit that supplies power to the sensor unit and the wireless communication unit; a determination unit that determines a level of transmission urgency of wireless transmission of the data; and a control unit that controls the wireless communication unit to wirelessly transmit the data, the control unit executing control to inhibit the wireless communication unit from using power supplied from the main power supply unit when causing the wireless communication unit to wirelessly transmit the data of which the transmission urgency is determined to be low by the determination unit.

The wireless terminal may further include: an auxiliary power supply unit that supplies power to the wireless communication unit. The determination unit may determine whether or not the power supplied from the auxiliary power supply unit is sufficient for the wireless communication unit to wirelessly transmit the data. The control unit may control the wireless communication unit to use the power supplied from the auxiliary power supply unit when causing the wireless communication unit to wirelessly transmit the data if the determination unit determines that the power supplied from the auxiliary power supply unit is sufficient.

The wireless terminal may further include: a retention unit that retains the data. The control unit may control the retention unit to retain the data of which the transmission urgency is determined to be low by the determination unit.

The determination unit may set a transmission time limit for the data retained in the retention unit and determine that the transmission urgency of the data of which the transmission time limit has been reached is high.

The determination unit may determine that the power supplied from the auxiliary power supply unit is sufficient while power is supplied from an outside to the auxiliary power supply unit.

The auxiliary power supply unit may have a rechargeable battery capable of being charged from an outside. The determination unit may determine that the power supplied from the auxiliary power supply unit is sufficient if the remaining charge of the rechargeable battery is greater than or equal to a predetermined amount.

According to the present invention, the determination unit determines a level of transmission urgency of wireless transmission of data. In addition, the control unit inhibits the wireless communication unit from using power supplied from the main power supply unit when controlling the wireless communication unit to wirelessly transmit data of which transmission urgency is determined to be low by the determination unit. Accordingly, it is possible to further suppress the power consumption of the main power supply unit.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

First Preferred Embodiment

Figure 1:
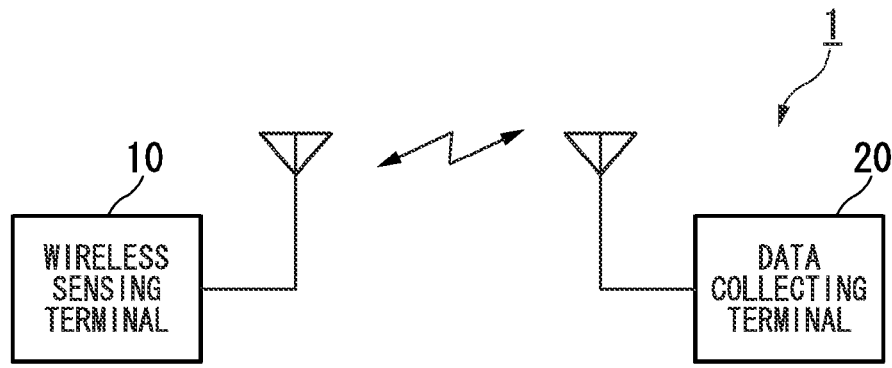
FIG. 1 is a schematic diagram illustrating a configuration of a biological data monitoring system in accordance with a first preferred embodiment of the present invention.

Hereinafter, the first preferred embodiment of the present invention will be described with reference to the drawings. FIG. 1 is a schematic diagram illustrating a configuration of a biological data monitoring system in accordance with the first preferred embodiment of the present invention. The biological data monitoring system 1 includes a wireless sensing terminal 10 and a data collecting terminal 20. The wireless sensing terminal 10 acquires biological data such as blood pressure, pulse, electrical activity of the heart, heart rate, blood oxygen concentration, body temperature, urinary sugar, or blood sugar from the surface of a human body or inside of a human body using various sensors. In addition, the wireless sensing terminal 10 acquires device sate data indicating states of parts provided in the wireless sensing terminal 10 using various sensors. In addition, the wireless sensing terminal 10 wirelessly transmits the acquired biological data and the device state data to the data collecting terminal 20. The data collecting terminal 20 collects and stores the biological data and the device state data wirelessly transmitted from the wireless sensing terminal 10. Although an example in which the wireless sensing terminal 10 and the data collecting terminal 20 perform one-to-one wireless communication has been described in the first preferred embodiment of the present invention, the present invention can be applied to any case of 1-to-N, M-to-1, and M-to-N, wherein N and M are natural numbers.

Figure 2:
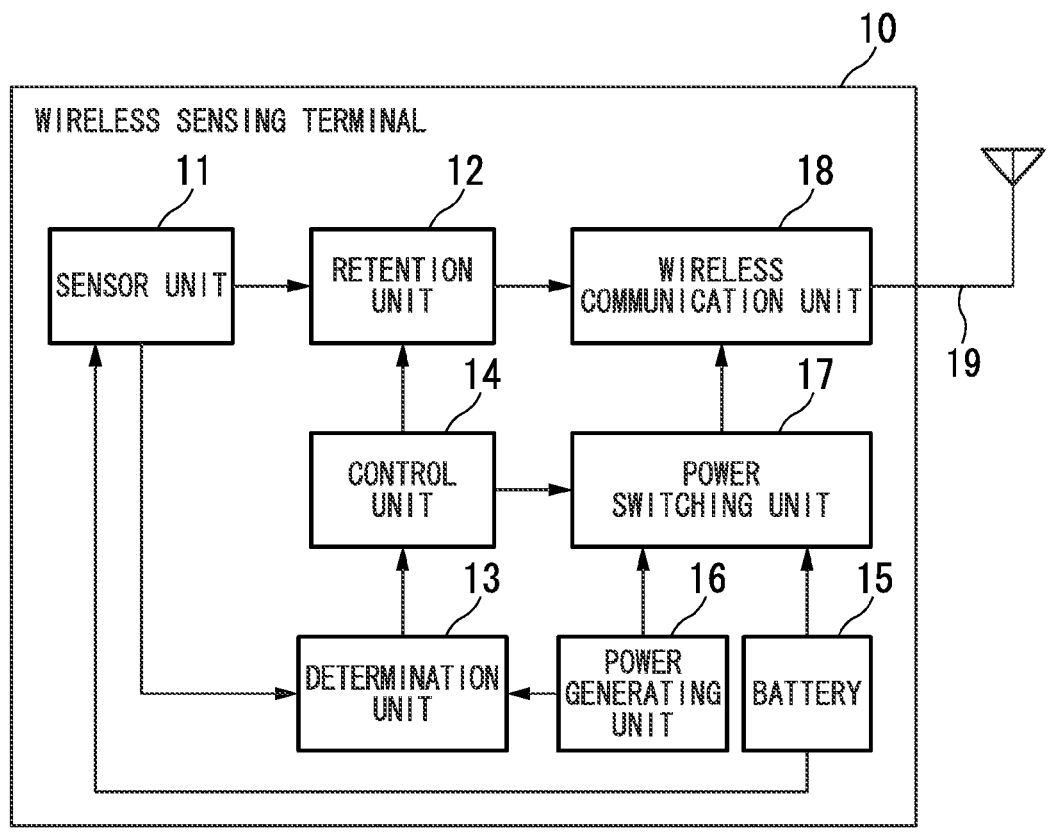
FIG. 2 is a block diagram illustrating a configuration of a wireless sensing terminal in accordance with the first preferred embodiment of the present invention.

Next, a configuration of the wireless sensing terminal 10 will be described. FIG. 2 is a block diagram illustrating the configuration of the wireless sensing terminal 10 in accordance with the first preferred embodiment of the present invention. In an example of FIG. 2, the wireless sensing terminal 10 includes a sensor unit 11, a retention unit 12, a determination unit 13, a control unit 14, a battery 15 (main power supply unit), a power generating unit 16 (auxiliary power supply unit), a power switching unit 17, a wireless communication unit 18, and an antenna 19.

The sensor unit 11 is installed on the human-body surface or inside the human body, and acquires biological data by sensing blood pressure, pulse, electrical activity of the heart, heart rate, blood oxygen concentration, body temperature, urinary sugar, blood sugar, or the like. In addition, the sensor unit 11 acquires device state data by sensing the states of the parts provided in the wireless sensing terminal 10 such as a voltage of electricity generated by the power generating unit 16 and the voltage of the battery 15. Hereinafter, the biological data, the device state data, or the like acquired by the sensor unit 11 is written as collected data. In addition, the sensor unit 11 outputs the collected data to the retention unit 12 and the determination unit 13. The sensor unit 11 assigns an identifier (ID) (hereinafter written as a common ID) for uniquely specifying data for the collection data.

The retention unit 12 acquires and retains the collected data output by the sensor unit 11, and outputs the retained collected data to the wireless communication unit 18 according to control of the control unit 14. The determination unit 13 acquires the collected data output by the sensor unit 11 and determines whether the acquired collected data is data of which transmission urgency is high or low. The data of which the transmission urgency is high needs to be immediately transmitted to the data collecting terminal 20, and the data of which the transmission urgency is low does not need to be immediately transmitted to the data collecting terminal 20. In addition, the determination unit 13 determines whether or not power generated by the power generating unit 16 is greater than or equal to power necessary for the wireless communication unit 18 to transmit data. A detailed operation of the determination unit 13 will be described later. The control unit 14 controls the parts provided in the wireless sensing terminal 10. A detailed operation of the control unit 14 will be described later.

The battery 15 is a primary battery, which supplies power to the sensor unit 11, and further supplies power to the wireless communication unit 18 based on an operation of the power switching unit 17. Electric energy capable of being supplied by the battery 15 is finite. The power generating unit 16 generates power using vibration, a temperature difference, light, electromagnetic waves, or the like, supplies power to the determination unit 13, and further supplies power to the wireless communication unit 18 based on an operation of the power switching unit 17. The power generating unit 16 may be configured to receive power supplied from the outside, to supply the power received from the outside to the determination unit 13, and to further supply the power to the wireless communication unit 18 based on an operation of the power switching unit 17. The power switching unit 17 performs an operation of supplying power output by either the battery 15 or the power generating unit 16 to the wireless communication unit 18 according to control of the control unit 14.

The wireless communication unit 18 acquires collected data output by the retention unit 12, and transmits the acquired collected data to the data collecting terminal 20 via the antenna 19 using power supplied from the battery 15 or the power generating unit 16.

Figure 3:
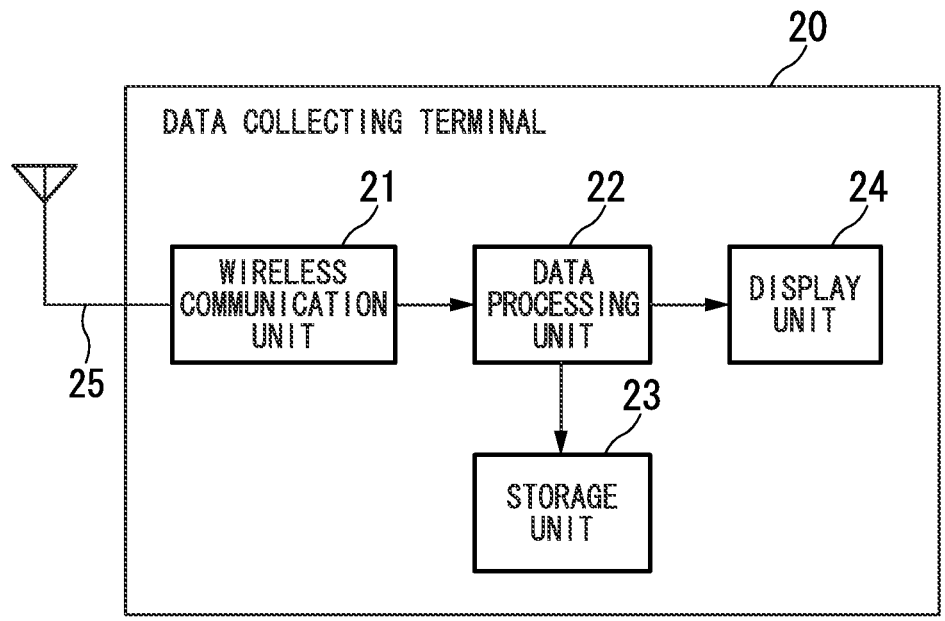
FIG. 3 is a block diagram illustrating a configuration of a data collecting terminal in accordance with the first preferred embodiment of the present invention.

Next, a configuration of the data collecting terminal 20 will be described. FIG. 3 is a block diagram illustrating the configuration of the data collecting terminal 20 in accordance with the first preferred embodiment of the present invention.

In an example of FIG. 3, the data collecting terminal 20 includes a wireless communication unit 21, a data processing unit 22, a storage unit 23, a display unit 24, and an antenna 25.

The wireless communication unit 21 receives collected data transmitted from the wireless sensing terminal 10 via the antenna 25, and outputs the received collected data to the data processing unit 22. The data processing unit 22 acquires the collected data output by the wireless communication unit 21. The data processing unit 22 generates storage data by converting a data format of the acquired collected data into a storage data format, outputs the generated storage data to the storage unit 23, converts the acquired collected data into display data such as text or an image, and outputs the display data into which a conversion has been performed to the display unit 24. The storage unit 23 stores the storage data output by the data processing unit 22. The display unit 24 displays the display data output by the data processing unit 22. According to this configuration, the data collecting terminal 20 can display the collected data transmitted from the wireless sensing terminal 10 on the display unit 24, and store the collected data in the storage unit 23.

Figure 4:
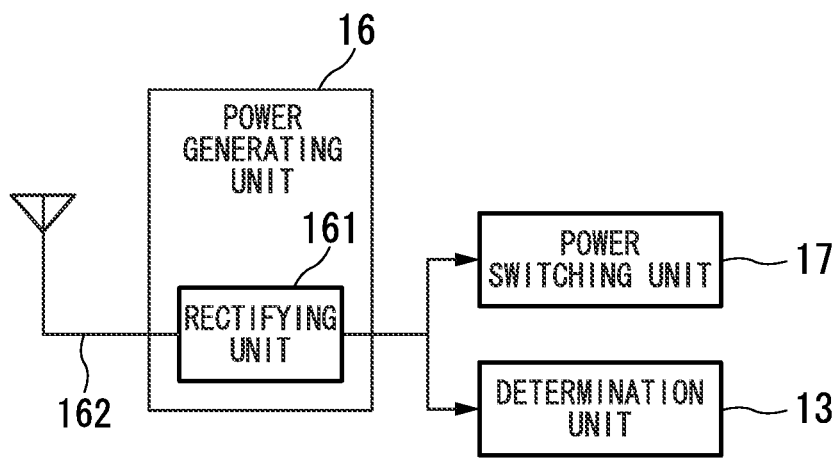
FIG. 4 is a block diagram illustrating a configuration of a power generating unit in accordance with the first preferred embodiment of the present invention.

Next, a configuration of the power generating unit 16 provided in the wireless sensing terminal 10 will be described. Although any device that generates power using vibration, a temperature difference, light, electromagnetic waves, or the like may be used as the power generating unit 16, an example of a configuration in which power is generated using the electromagnetic waves will be described here. FIG. 4 is a block diagram illustrating the configuration of the power generating unit 16 in accordance with the first preferred embodiment of the present invention. In an example of FIG. 4, the power generating unit 16 includes a rectifying unit 161 and an antenna 162. The power generating unit 16, which generates the power using the electromagnetic waves, generates power (direct current (DC) power) by rectifying the electromagnetic waves (alternating current (AC) signal) received by the antenna 162 in the rectifying circuit 161 to generate DC.

Figure 5:
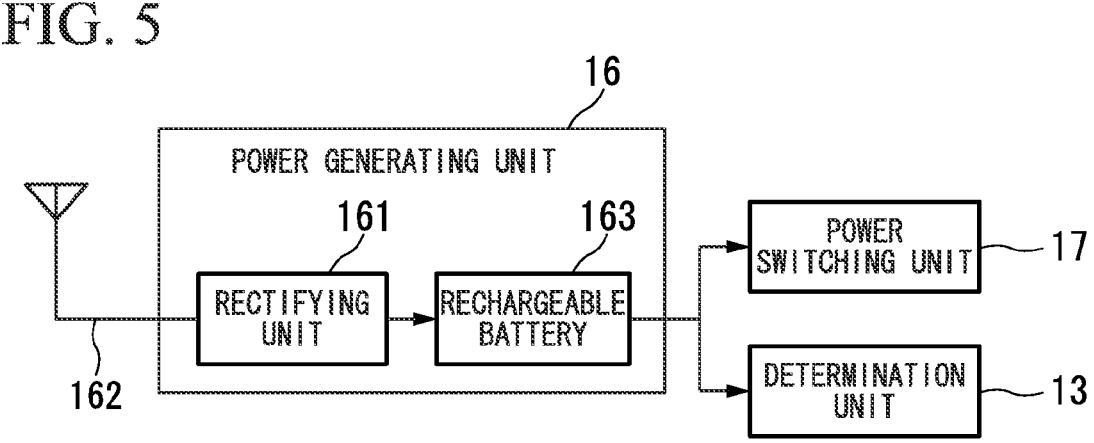
FIG. 5 is a block diagram illustrating a configuration of a power generating unit including a rechargeable battery in accordance with the first preferred embodiment of the present invention.

The power generating unit 16 may include a rechargeable battery (secondary battery), and supply power from the rechargeable battery to an outside by accumulating the generated power in the rechargeable battery. FIG. 5 is a block diagram illustrating the configuration of the power generating unit 16 including the rechargeable battery in accordance with the first preferred embodiment of the present invention. In an example of FIG. 5, the power generating unit 16 includes the rectifying unit 161, the antenna 162, and a rechargeable battery 163. The power generating unit 16 including the rechargeable battery 163 accumulates the generated power in the rechargeable battery 163. If the power generating unit 16 is configured to include the rechargeable battery 163 and output power from the rechargeable battery 163 as described above, it is possible to further improve usability because power previously accumulated in the rechargeable battery 163 can be supplied to the wireless communication unit 18 even when the rectifying unit 161 supplies only power insufficient to perform non-output or wireless communication when the wireless communication unit 18 performs wireless communication.

Figures 6, 7:
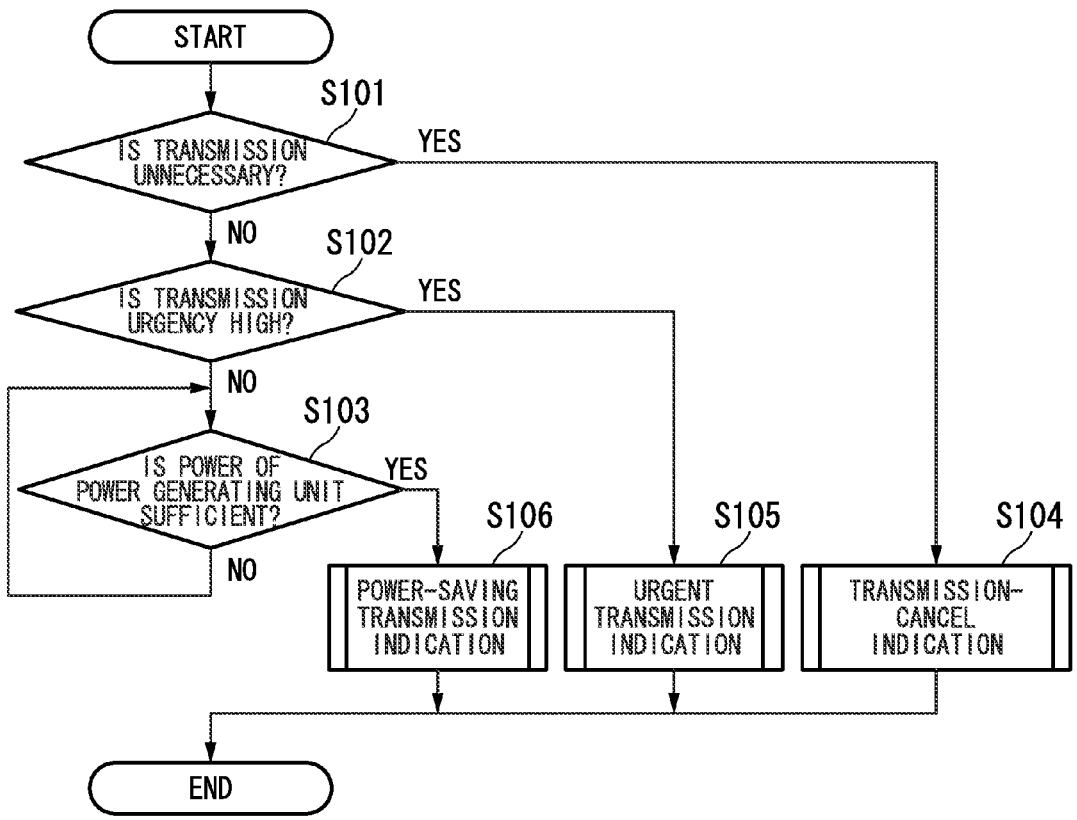
FIG. 6 is a flowchart illustrating a processing procedure of a determination unit in accordance with the first preferred embodiment of the present invention.
FIG. 7 is a diagram illustrating an operation of a control unit corresponding to an indication input from a determination unit in the form of a table in accordance with the first preferred embodiment of the present invention.

Next, a detailed processing procedure of the determination unit 13 will be described. FIG. 6 is a flowchart illustrating the processing procedure of the determination unit 13 in accordance with the first preferred embodiment of the present invention.

(Step S101)

The determination unit 13 executes a transmission necessity determination step when acquiring collected data output by the sensor unit 11. In the transmission necessity determination step, the determination unit 13 determines whether or not the acquired collected data does not need to be transmitted to the data collecting terminal 20. If the determination unit 13 determines that the acquired collected data does not need to be transmitted to the data collecting terminal 20, it proceeds to the process of step S104. If the determination unit 13 determines that the acquired collected data needs to be transmitted, it proceeds to the process of step S102. For example, if the collected data output by the sensor unit 11 is data indicating that the wireless sensing terminal 10 operates normally, the determination unit 13 determines that the data does not need to be transmitted to the data collecting terminal 20. In the case of other data, the determination unit 13 determines that the data needs to be transmitted to the data collecting terminal 20. A standard of whether or not the data needs to be transmitted to the data collecting terminal 20 may be predefined or arbitrarily set.

(Step S102)

The determination unit 13 executes a transmission urgency determination step. In the transmission urgency determination step, the determination unit 13 determines whether or not the collected data determined to be transmitted in the process of step S101 is data of which transmission urgency is high. If the determination unit 13 determines that the collected data determined to be transmitted in the process of step S101 is the data of which the transmission urgency is high, it proceeds to the process of step S105. If the determination unit 13 determines that the collected data is the data of which the transmission urgency is low, it proceeds to the process of step S103. For example, if the collected data determined to be transmitted in the process of step S101 is pulse data and a pulse value is less than a predetermined value (less than a normal value), the determination unit 13 determines that it is the data of which the transmission urgency is high. If the pulse value is greater than or equal to the predetermined value, it is determined to be the data of which the transmission urgency is low. A standard of a level of transmission urgency may be predefined or arbitrarily set. When it proceeds to the process of step S103, the control unit 14 controls the retention unit 12 to directly retain the collected data retained by the retention unit 12.

(Step S103)

The determination unit 13 executes a power determination step. In the power determination step, the determination unit 13 determines whether or not power generated by the power generating unit 16 is greater than or equal to power necessary for the wireless communication unit 18 to transmit data (whether or not the power generated by the power generating unit 16 is greater than or equal to a standard value). Specifically, the determination unit 13 detects a voltage of the power generated by the power generating unit 16, and compares the detected voltage to a preset threshold. If the voltage of the electricity generated by the power generating unit 16 is greater than or equal to the threshold, the determination unit 13 proceeds to the process of step S106 by determining that the power generated by the power generating unit 16 is greater than or equal to the power necessary for the wireless communication unit 18 to transmit data. In addition, if the voltage of the electricity generated by the power generating unit 16 is less than the threshold, the determination unit 13 re-executes the process of step S103 by determining that the power generated by the power generating unit 16 is less than the power necessary for the wireless communication unit 18 to transmit data.

If the power generating unit 16 includes the rechargeable battery 163 and the remaining charge of the rechargeable battery 163 is greater than or equal to a predetermined amount in the power determination step, the power generated by the power generating unit 16 may be determined to be greater than or equal to the power necessary for the wireless communication unit 18 to transmit data. In addition, if the power generating unit 16 is configured to receive power supplied from an outside, the power generated by the power generating unit 16 may be determined to be greater than or equal to the power necessary for the wireless communication unit 18 to transmit data while the power generating unit 16 receives the power supplied from the outside in the power determination step.

(Step S104)

The determination unit 13 outputs a transmission-cancel indication indicating that the transmission of the collected data has not been performed and a common ID attached to the collected data acquired in the process of step S101 to the control unit 14. Thereafter, the process ends.

(Step S105)

The determination unit 13 outputs an urgent transmission indication indicating that the collected data is transmitted using power supplied by the battery 15 and the common ID attached to the collected data acquired in the process of step S101 to the control unit 14. Thereafter, the process ends.

(Step S106)

The determination unit 13 outputs a power-saving transmission indication indicating that the collected data is transmitted using power generated by the power generating unit 16 and the common ID attached to the collected data acquired in the process of step S101 to the control unit 14. Thereafter, the process ends.

Next, an operation of the control unit 14 when the "urgent transmission indication," the "power-saving transmission indication," and the "transmission-cancel indication" are each input from the determination unit 13 will be described. FIG. 7 is a diagram illustrating the operation of the control unit 14 corresponding to the indication input from the determination unit 13 in the form of a table in accordance with the first preferred embodiment of the present invention. In example of FIG. 7, the indication input from the determination unit 13 is associated with control content for the retention unit 12 and control content for the power switching unit 17 for which the control unit 14 operates based on the indication input from the determination unit 13.

Specifically, when the "urgent transmission indication" and the "common ID" are input from the determination unit 13, the control unit 14 controls the retention unit 12 to output the collected data specified by the common ID to the wireless communication unit 18, and controls the power switching unit 17 to supply power output by the battery 15 to the wireless communication unit 18. According to the above-described control, the wireless communication unit 18 transmits the collected data specified by the common ID to the data collecting terminal 20 using the power supplied from the battery 15.

In addition, when the "power-saving transmission indication" and the "common ID" are input from the determination unit 13, the control unit 14 controls the retention unit 12 to output the collected data specified by the common ID to the wireless communication unit 18, and controls the power switching unit 17 to inhibit the wireless communication unit 18 from using the power supplied from the battery 15 and supply the power generated by the power generating unit 16 to the wireless communication unit 18. According to the above-described control, the wireless communication unit 18 transmits the collected data specified by the common ID to the data collecting terminal 20 using the power generated by the power generating unit 16.

In addition, when the "transmission-cancel indication" and the "common ID" are input from the determination unit 13, the control unit 14 causes the retention unit 12 to delete the collected data specified by the common ID. According to the above-described control, the collected data specified by the common ID is deleted without being transmitted to the data collecting terminal 20.

According to the above-described configuration and process, when data of which the transmission urgency is low is transmitted to the data collecting terminal 20, the wireless sensing terminal 10 can be inhibited from using the power supplied by the battery 15 and operate using the power generated by the power generating unit 16. Accordingly, the wireless sensing terminal 10 can suppress the power consumption of the battery 15 of which electric energy capable of being supplied is finite.

Second Preferred Embodiment

Next, the second preferred embodiment of the present invention will be described with reference to the drawings. Configurations of a wireless sensing terminal 10 and a data collecting terminal 20 in accordance with the second preferred embodiment of the present invention are the same as those of devices of the first preferred embodiment. A difference between the second preferred embodiment and the first preferred embodiment of the present invention is that, in the second preferred embodiment of the present invention, transmission is performed using power generated by the power generating unit 16 without performing the transmission using power supplied by the battery 15 if the power generated by the power generating unit 16 is sufficient when collected data of which transmission urgency is high is transmitted. The control unit 14 performs the same operation as the control unit 14 in accordance with the first preferred embodiment.

Figure 8:
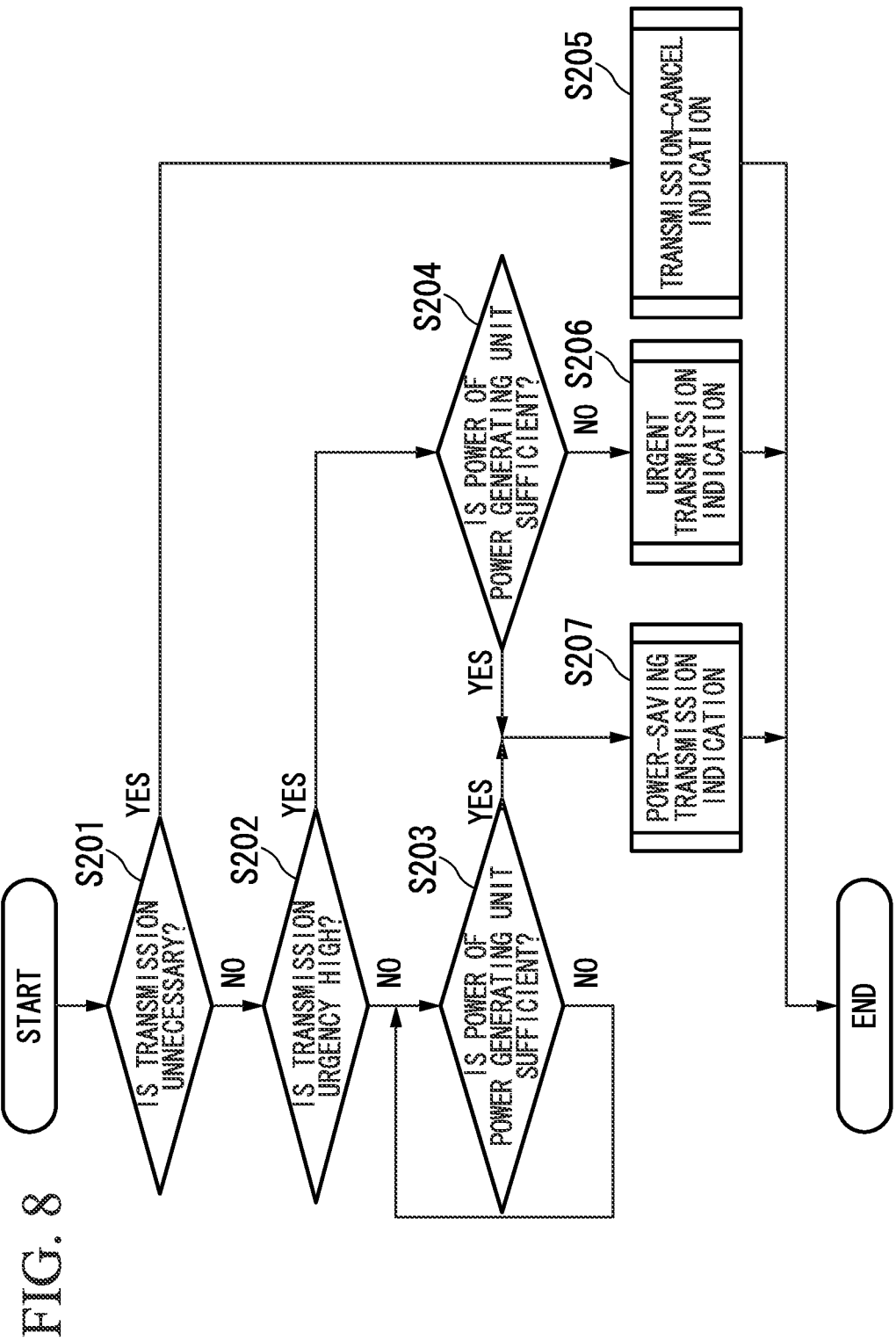
FIG. 8 is a flowchart illustrating processing procedures of a determination unit in accordance with a second preferred embodiment of the present invention.

Next, a detailed processing procedure of the determination unit 13 will be described. FIG. 8 is a flowchart illustrating the processing procedure of the determination unit 13 in accordance with the second preferred embodiment of the present invention.

(Step S201)

The determination unit 13 executes a transmission necessity determination step when acquiring collected data output by the sensor unit 11. A process of the transmission necessity determination step is the same as that of the transmission necessity determination step in accordance with the first preferred embodiment. If the determination unit 13 determines that the acquired collected data does not need to be transmitted to the data collecting terminal 20, it proceeds to the process of step S205. If the determination unit 13 determines that the acquired collected data needs to be transmitted, it proceeds to the process of step S202.

(Step S202)

The determination unit 13 executes a transmission urgency determination step. The process of the transmission urgency determination step is the same as that of the transmission urgency determination step in accordance with the first preferred embodiment. If the determination unit 13 determines that the collected data determined to be transmitted in the process of step S201 is the data of which the transmission urgency is high, it proceeds to the process of step S204. If the determination unit 13 determines that the collected data is the data of which the transmission urgency is low, it proceeds to the process of step S203.

(Step S203)

The determination unit 13 executes a power determination step. A process of the power determination step is the same as that of the power determination step in accordance with the first preferred embodiment. The determination unit 13 detects a voltage of electricity generated by the power generating unit 16, and compares the detected voltage to a preset threshold. If the voltage of the power generated by the power generating unit 16 is greater than or equal to the threshold, the determination unit 13 proceeds to the process of step S207 by determining that the power generated by the power generating unit 16 is greater than or equal to power necessary for the wireless communication unit 18 to transmit data. If the voltage of the power generated by the power generating unit 16 is less than the threshold, the determination unit 13 re-executes the process of step S203 by determining that the power generated by the power generating unit 16 is less than the power necessary for the wireless communication unit 18 to transmit data.

(Step S204)

The determination unit 13 executes the same power determination step as in the process of step S203. The determination unit 13 detects the voltage of the power generated by the power generating unit 16, and compares the detected voltage to the preset threshold. If the voltage of the power generated by the power generating unit 16 is greater than or equal to the threshold, the determination unit 13 proceeds to the process of step S207 by determining that the power generated by the power generating unit 16 is greater than or equal to the power necessary for the wireless communication unit 18 to transmit data. If the voltage of the power generated by the power generating unit 16 is less than the threshold, the determination unit 13 proceeds to the process of step S206 by determining that the power generated by the power generating unit 16 is less than the power necessary for the wireless communication unit 18 to transmit data.

(Step S205)

The determination unit 13 outputs a transmission-cancel indication indicating that the transmission of the collected data has not been performed and also outputs a common ID attached to the collected data acquired in the process of step S201 to the control unit 14. Thereafter, the process ends.

(Step S206)

The determination unit 13 outputs an urgent transmission indication indicating that the collected data is transmitted using power supplied by the battery 15 and the common ID attached to the collected data acquired in the process of step S201 to the control unit 14. Thereafter, the process ends.

(Step S207)

The determination unit 13 outputs a power-saving transmission indication indicating that the collected data is transmitted using the power generated by the power generating unit 16 and the common ID attached to the collected data acquired in the process of step S201 to the control unit 14. Thereafter, the process ends.

According to the above-described configuration and process, when data of which the transmission urgency is low is transmitted to the data collecting terminal 20, the wireless sensing terminal 10 can be inhibited from using the power supplied by the battery 15 and operate using the power generated by the power generating unit 16. Accordingly, the wireless sensing terminal 10 can suppress the power consumption of the battery 15 of which electric energy capable of being supplied is finite. Further, in this preferred embodiment, it is possible to use the power generated by the power generating unit 16 without using the power supplied by the battery 15 if the power generated by the power generating unit 16 is sufficient when data of which the transmission urgency is high is transmitted by executing the process of step S204. Accordingly, the wireless sensing terminal 10 can further suppress the power consumption of the battery 15 of which electric energy capable of being supplied is finite.

Third Preferred Embodiment

Next, the third preferred embodiment of the present invention will be described with reference to the drawings. A configuration of the data collecting terminal 20 in accordance with the third preferred embodiment of the present invention is the same as that of the data collecting terminal 20 of the first preferred embodiment. A difference between the third preferred embodiment and the first preferred embodiment of the present invention is that the wireless sensing terminal includes a timer unit and collected data exceeding a transmission time limit is transmitted using power supplied by the battery 15 in the third preferred embodiment of the present invention. The control unit 14 performs the same operation as the control unit 14 in accordance with the first preferred embodiment.

Figure 9:
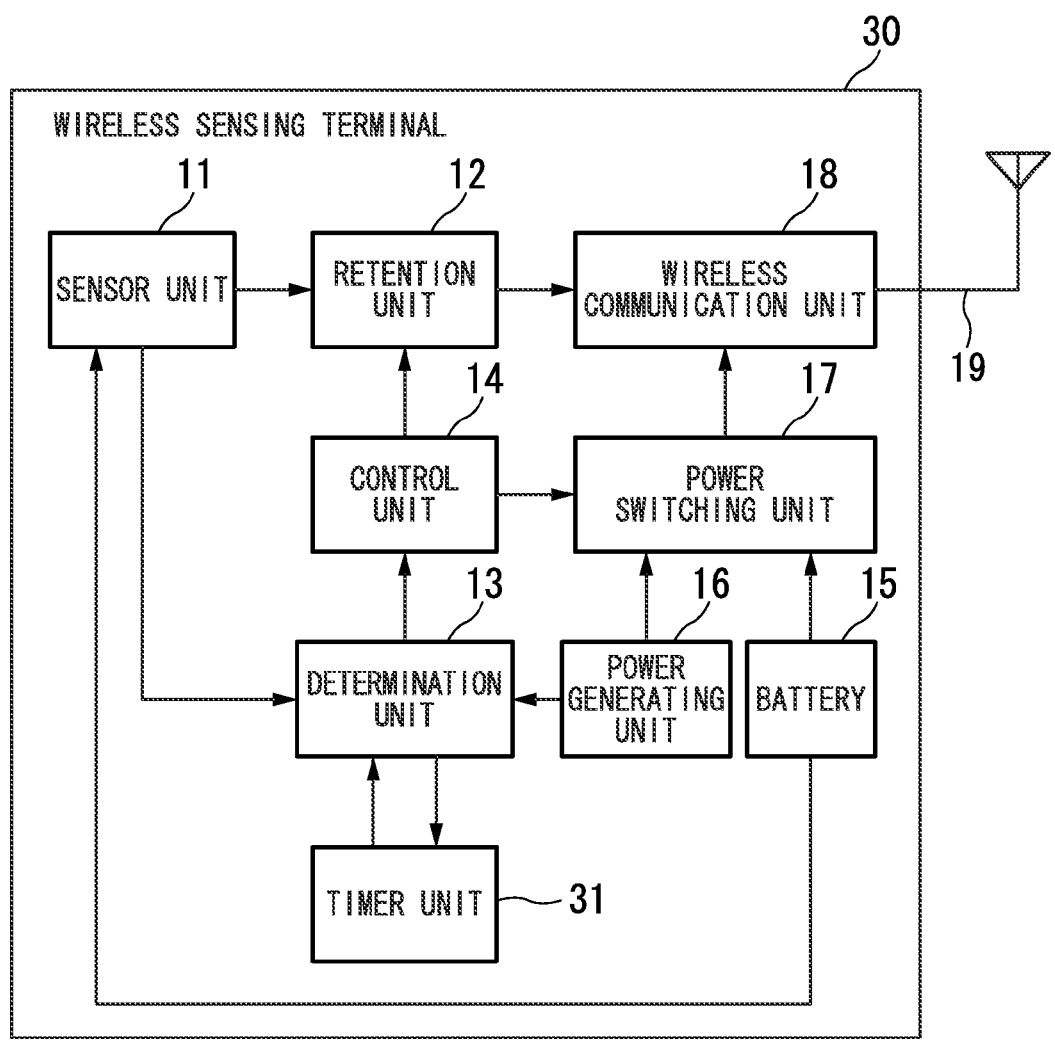
FIG. 9 is a block diagram illustrating a configuration of a wireless sensing terminal in accordance with a third preferred embodiment of the present invention.

Next, a configuration of the wireless sensing terminal will be described. FIG. 9 is a block diagram illustrating the configuration of a wireless sensing terminal 30 in accordance with the third preferred embodiment of the present invention. In an example of FIG. 9, the wireless sensing terminal 30 includes the sensor unit 11, the retention unit 12, the determination unit 13, the control unit 14, the battery 15, the power generating unit 16, the power switching unit 17, the wireless communication unit 18, the antenna 19, and a timer unit 31.

The sensor unit 11, the retention unit 12, the determination unit 13, the control unit 14, the battery 15, the power generating unit 16, the power switching unit 17, the wireless communication unit 18, and the antenna 19 are the same as the parts in accordance with the first preferred embodiment. Based on an indication from the determination unit 13, the timer unit 31 sets a transmission time limit for collected data that is not yet transmitted, and outputs a transmission time-limit arrival notification to the determination unit when the transmission time limit has been reached.

Figure 10:
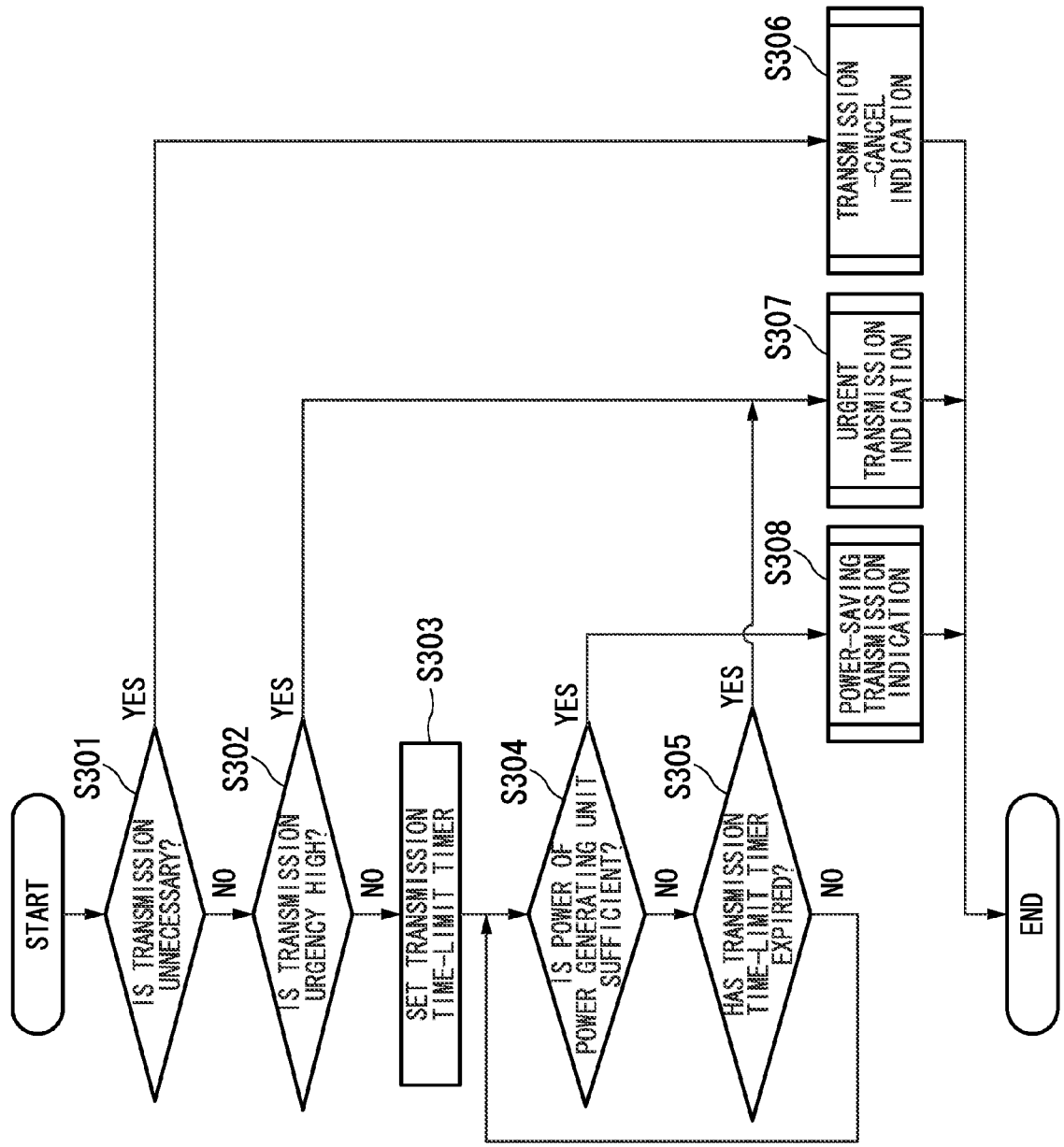
FIG. 10 is a flowchart illustrating processing procedures of a determination unit and a timer unit in accordance with the third preferred embodiment of the present invention.

Next, detailed processing procedures of the determination unit 13 and the timer unit 31 will be described. FIG. 10 is a flowchart illustrating the processing procedures of the determination unit 13 and the timer unit 31 in accordance with the third preferred embodiment of the present invention.

(Step S301)

The determination unit 13 executes a transmission necessity determination step when acquiring collected data output by the sensor unit 11. A process of the transmission necessity determination step is the same as that of the transmission necessity determination step in accordance with the first preferred embodiment. If the determination unit 13 determines that the acquired collected data does not need to be transmitted to the data collecting terminal 20, it proceeds to the process of step S306. If the determination unit 13 determines that the acquired collected data needs to be transmitted, it proceeds to the process of step S302.

(Step S302)

The determination unit 13 executes a transmission urgency determination step. A process of the transmission urgency determination step is the same as that of the transmission urgency determination step in accordance with the first preferred embodiment. If the determination unit 13 determines that the collected data determined to be transmitted in the process of step S301 is data of which the transmission urgency is high, it proceeds to the process of step S307. If the determination unit 13 determines that the collected data is the data of which the transmission urgency is low, it proceeds to the process of step S303.

(Step S303)

The timer unit 31 sets a transmission time limit for the collected data determined to be the data of which the transmission urgency is low in the process of step S302. Thereafter, it proceeds to the process of step S304. For example, when it is necessary to periodically transmit the collected data to the data collecting terminal 20 once per hour for state monitoring, the transmission time limit is determined to be "one hour."

(Step S304)

The determination unit 13 executes a power determination step. A process of the power determination step is the same as that of the power determination step in accordance with the first preferred embodiment. The determination unit 13 detects a voltage of electricity generated by the power generating unit 16, and compares the detected voltage to a preset threshold. If the voltage of the power generated by the power generating unit 16 is greater than or equal to the threshold, the determination unit 13 proceeds to the process of step S308 by determining that the power generated by the power generating unit 16 is greater than or equal to power necessary for the wireless communication unit 18 to transmit data. If the voltage of the power generated by the power generating unit 16 is less than the threshold, the determination unit 13 proceeds to the process of step S305 by determining that the power generated by the power generating unit 16 is less than the power necessary for the wireless communication unit 18 to transmit data.

(Step S305)

The determination unit 13 executes a transmission time-limit expiration determination step. In the transmission time-limit expiration determination step, the determination unit 13 determines whether or not the transmission time limit of the collected data set in step S303 has expired based on the transmission time-limit arrival notification output by the timer unit 31. Because the timer unit 31 outputs the transmission time-limit arrival notification to the determination unit 13 when the transmission time limit has been reached, the determination unit 13 determines that the transmission time limit has expired when acquiring the transmission time-limit arrival notification output by the timer unit 31. Otherwise, the determination unit 13 determines that the transmission time limit has not expired. When determining that the transmission time limit of the collected data set in step S303 has expired, the determination unit 13 proceeds to the process of step S307 by determining that the collected data of which the transmission time limit has expired is data of which the transmission urgency is high. Otherwise, the determination unit 13 returns to the process of step S304.

(Step S306)

The determination unit 13 outputs a transmission-cancel indication indicating that the transmission of the collected data has not been performed and also outputs a common ID attached to the collected data acquired in the process of step S301 to the control unit 14. Thereafter, the process ends.

(Step S307)

The determination unit 13 outputs an urgent transmission indication indicating that the collected data is transmitted using the power supplied by the battery 15 and the common ID attached to the collected data acquired in the process of step S301 to the control unit 14. Thereafter, the process ends.

(Step S308)

The determination unit 13 outputs a power-saving transmission indication indicating that the collected data is transmitted using the power generated by the power generating unit 16 and the common ID attached to the collected data acquired in the process of step S301 to the control unit 14. Thereafter, the process ends.

According to the above-described configuration and process, when data of which the transmission urgency is low is transmitted to the data collecting terminal 20, the wireless sensing terminal 30 can be inhibited from using the power supplied by the battery 15 and operate using the power generated by the power generating unit 16. In addition, the wireless sensing terminal 30 also transmits the data of which the transmission urgency is low using the power supplied by the battery 15 when its transmission time limit has elapsed. For example, even when the power generated by the power generating unit 16 is low and a period in which the collected data of which the transmission urgency is low is not transmitted is continuous during a fixed period, transmission is performed using the power supplied by the battery 15 when the transmission time limit has elapsed. Accordingly, the wireless sensing terminal 30 can also necessarily transmit the collected data of which the transmission urgency is low when its transmission time limit has elapsed while suppressing the power consumption of the battery 15 of which electric energy capable of being supplied is finite.

Fourth Preferred Embodiment

Next, the fourth preferred embodiment of the present invention will be described with reference to the drawings. Configurations of the wireless sensing terminal 30 and the data collecting terminal 20 in accordance with the fourth preferred embodiment of the present invention are the same as those of the devices of the third preferred embodiment. A difference between the fourth preferred embodiment and the third preferred embodiment of the present invention is that transmission is performed using power generated by the power generating unit 16 without performing the transmission using power supplied by the battery 15 if the power generated by the power generating unit 16 is sufficient when collected data of which transmission urgency is high is transmitted in the fourth preferred embodiment of the present invention. The control unit 14 performs the same operation as the control unit 14 in accordance with the first preferred embodiment.

Figure 11:
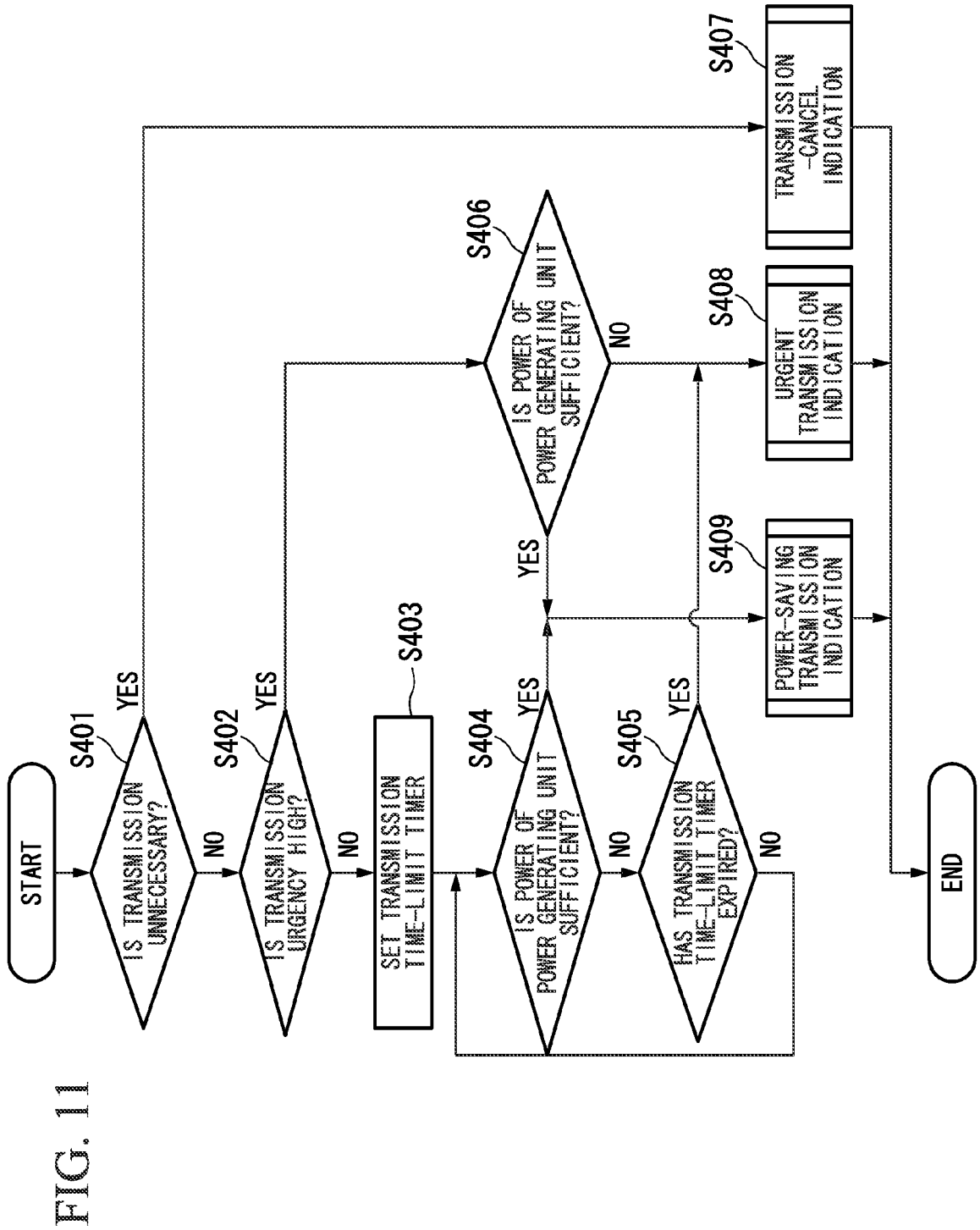
FIG. 11 is a flowchart illustrating processing procedures of a determination unit and a timer unit in accordance with a fourth preferred embodiment of the present invention.

Next, detailed processing procedures of the determination unit 13 and the timer unit 31 will be described. FIG. 11 is a flowchart illustrating the processing procedures of the determination unit 13 and the timer unit 31 in accordance with the fourth preferred embodiment of the present invention.

(Step S401)

The determination unit 13 executes a transmission necessity determination step when acquiring collected data output by the sensor unit 11. A process of the transmission necessity determination step is the same as that of the transmission necessity determination step in accordance with the first preferred embodiment. If the determination unit 13 determines that the acquired collected data does not need to be transmitted to the data collecting terminal 20, it proceeds to the process of step S407. If the determination unit 13 determines that the acquired collected data needs to be transmitted, it proceeds to the process of step S402.

(Step S402)

The determination unit 13 executes a transmission urgency determination step. A process of the transmission urgency determination step is the same as that of the transmission urgency determination step in accordance with the first preferred embodiment. If the determination unit 13 determines that the collected data determined to be transmitted in the process of step S401 is data of which the transmission urgency is high, it proceeds to the process of step S406. If the determination unit 13 determines that the collected data is the data of which the transmission urgency is low, it proceeds to the process of step S403.

(Step S403)

The timer unit 31 sets a transmission time limit for the collected data determined to be the data of which the transmission urgency is low in the process of step S402. Thereafter, it proceeds to the process of step S404.

(Step S404)

The determination unit 13 executes a power determination step. A process of the power determination step is the same as that of the power determination step in accordance with the first preferred embodiment. The determination unit 13 detects a voltage of electricity generated by the power generating unit 16, and compares the detected voltage to a preset threshold. If the voltage of the electricity generated by the power generating unit 16 is greater than or equal to the threshold, the determination unit 13 proceeds to the process of step S409 by determining that the power generated by the power generating unit 16 is greater than or equal to power necessary for the wireless communication unit 18 to transmit data. If the voltage of the electricity generated by the power generating unit 16 is less than the threshold, the determination unit 13 proceeds to the process of step S405 by determining that the power generated by the power generating unit 16 is less than the power necessary for the wireless communication unit 18 to transmit data.

(Step S405)

The determination unit 13 executes a transmission time-limit expiration determination step. A process of the transmission time-limit expiration determination step is the same as that of the transmission time-limit expiration determination step in accordance with the third preferred embodiment. When determining that the transmission time limit of the collected data set in step S403 has expired, the determination unit 13 proceeds to the process of step S408 by determining that the collected data of which the transmission time limit has expired is data of which the transmission urgency is high. Otherwise, the determination unit 13 returns to the process of step S404.

(Step S406)

The determination unit 13 executes the same power determination step as in the process of step S404. The determination unit 13 detects the voltage of the power generated by the power generating unit 16, and compares the detected voltage to the preset threshold. If the voltage of the power generated by the power generating unit 16 is greater than or equal to the threshold, the determination unit 13 proceeds to the process of step S409 by determining that the power generated by the power generating unit 16 is greater than or equal to the power necessary for the wireless communication unit 18 to transmit data. If the voltage of the power generated by the power generating unit 16 is less than the threshold, the determination unit 13 proceeds to the process of step S408 by determining that the power generated by the power generating unit 16 is less than the power necessary for the wireless communication unit 18 to transmit data.

(Step S407)

The determination unit 13 outputs a transmission-cancel indication indicating that the transmission of the collected data is not performed and a common ID attached to the collected data acquired in the process of step S401 to the control unit 14. Thereafter, the process ends.

(Step S408)

The determination unit 13 outputs an urgent transmission indication indicating that the collected data is transmitted using the power supplied by the battery 15 and the common ID attached to the collected data acquired in the process of step S401 to the control unit 14. Thereafter, the process ends.

(Step S409)

The determination unit 13 outputs a power-saving transmission indication indicating that the collected data is transmitted using the power generated by the power generating unit 16 and the common ID attached to the collected data acquired in the process of step S401 to the control unit 14. Thereafter, the process ends.

According to the above-described configuration and process, when data of which the transmission urgency is low is transmitted to the data collecting terminal 20, the wireless sensing terminal 30 can be inhibited from using the power supplied by the battery 15 and operate using the power generated by the power generating unit 16. In addition, the wireless sensing terminal 30 also transmits the data of which the transmission urgency is low using the power supplied by the battery 15 when its transmission time limit has elapsed. Accordingly, the wireless sensing terminal 30 can also necessarily transmit collected data of which the transmission urgency is low when its transmission time limit has elapsed while suppressing the power consumption of the battery 15 of which electric energy capable of being supplied is finite.

Further, in the fourth preferred embodiment of the present invention, it is possible to use the power generated by the power generating unit 16 without using the power supplied by the battery 15 if the power generated by the power generating unit 16 is sufficient when data of which the transmission urgency is high is transmitted by executing the process of step S406. Accordingly, the wireless sensing terminal 30 can further suppress the power consumption of the battery 15 of which electric energy capable of being supplied is finite.

While preferred embodiments of the present invention have been described and illustrated above, it should be understood that these are examples of the present invention and are not to be considered as limiting. Additions, omissions, substitutions, and other modifications can be made without departing from the scope of the present invention. Although an example in which the wireless sensing terminal and the data collecting terminal perform one-to-one wireless communication has been described in the first to fourth preferred embodiments of the present invention, the present invention is applicable to a relationship of 1-to-N, M-to-1, or M-to-N (N and M are natural numbers). In addition, although the battery 15 supplies power to the sensor unit 11 in the first to fourth preferred embodiments, the power generating unit 16 may supply power to the sensor unit 11. Accordingly, the invention is not to be considered as being limited by the foregoing description, and is only limited by the scope of the claims.

What is claimed is:

1. A wireless terminal comprising:
a sensor unit that generates data;
a wireless communication unit that wirelessly transmits the data;
a main power supply unit that supplies power to the sensor unit and the wireless communication unit;
a determination unit that determines a level of transmission urgency of wireless transmission of the data; and
a control unit that controls the wireless communication unit to wirelessly transmit the data, the control unit executing control to inhibit the wireless communication unit from using power supplied from the main power supply unit, regardless of remaining electric energy of the main power supply unit, when controlling the wireless communication unit to wirelessly transmit the data of which the transmission urgency is determined to be low by the determination unit.

2. The wireless terminal according to claim 1, further comprising:
an auxiliary power supply unit that supplies power to the wireless communication unit,
wherein the determination unit determines whether or not the power supplied from the auxiliary power supply unit is sufficient for the wireless communication unit to wirelessly transmit the data, and
the control unit controls the wireless communication unit to use the power supplied from the auxiliary power supply unit when controlling the wireless communication unit to wirelessly transmit the data if the determination unit determines that the power supplied from the auxiliary power supply unit is sufficient.

3. The wireless terminal according to claim 1, further comprising:
a retention unit that retains the data,
wherein the control unit controls the retention unit to retain the data of which the transmission urgency is determined to be low by the determination unit.

4. The wireless terminal according to claim 3, wherein the determination unit sets a transmission time limit for the data retained in the retention unit and determines that the transmission urgency of the data of which the transmission time limit has been reached is high.

5. The wireless terminal according to claim 2, wherein the determination unit determines that the power supplied from the auxiliary power supply unit is sufficient while power is supplied from an outside to the auxiliary power supply unit.

6. The wireless terminal according to claim 2, wherein:
the auxiliary power supply unit has a rechargeable battery capable of being charged from an outside, and
the determination unit determines that the power supplied from the auxiliary power supply unit is sufficient if the remaining charge of the rechargeable battery is greater than or equal to a predetermined amount.

* * * * *